United States Patent [19]

Melvin et al.

[11] Patent Number: 4,891,042
[45] Date of Patent: Jan. 2, 1990

[54] PORTABLE TAMPON APPLICATOR

[75] Inventors: Wayne D. Melvin, Camden; Jamshid Rejai, Dover, both of Del.

[73] Assignee: Playtex Family Products, Inc., Stamford, Conn.

[21] Appl. No.: 191,313

[22] Filed: May 6, 1988

[51] Int. Cl.$^4$ .............................................. A61F 13/20
[52] U.S. Cl. ......................................... 604/18; 604/16
[58] Field of Search ........................... 604/11, 13–16, 604/18

[56] References Cited

U.S. PATENT DOCUMENTS

| | | | |
|---|---|---|---|
| 2,587,717 | 3/1952 | Fourness | 604/18 |
| 3,101,713 | 8/1963 | Sargent . | |
| 3,534,737 | 10/1970 | Jones | 604/18 |
| 3,645,263 | 2/1972 | Bates | 604/18 |
| 3,895,634 | 7/1975 | Berger et al. . | |
| 4,273,125 | 6/1981 | Sakurai . | |
| 4,276,881 | 7/1981 | Lilaonitkul . | |
| 4,286,595 | 9/1981 | Ring | 604/18 |
| 4,291,696 | 9/1981 | Ring . | |
| 4,329,991 | 5/1982 | Sakurai . | |
| 4,411,647 | 10/1983 | Sakurai et al. . | |
| 4,479,791 | 10/1984 | Sprague . | |
| 4,498,899 | 2/1985 | Gross . | |
| 4,543,086 | 9/1985 | Johnson . | |
| 4,573,963 | 3/1986 | Sheldon | 604/15 |
| 4,650,459 | 3/1987 | Sheldon | 604/15 |
| 4,676,773 | 6/1987 | Sheldon . | |
| 4,699,610 | 10/1987 | Hanano et al. . | |
| 4,726,805 | 2/1988 | Sanders, III . | |

FOREIGN PATENT DOCUMENTS

| | | | |
|---|---|---|---|
| 0223072 | 5/1987 | European Pat. Off. . | |
| 684290 | 12/1952 | United Kingdom | 604/18 |
| 2033754A | 5/1980 | United Kingdom . | |

Primary Examiner—C. Fred Rosenbaum
Assistant Examiner—Mark O. Polutta
Attorney, Agent, or Firm—Stewart J. Fried

[57] ABSTRACT

A compact and short tampon applicator is formed of an outer barrel which surrounds a tampon-holding inner tubular plunger. The barrel has a pair of opposed tongues formed from portions of the wall of the outer barrel which are partially cut and deflected inwardly. The openings in the wall of the barrel provide effective means for holding the barrel during the insertion process. The tongues project into the interior of the plunger, through a pair of elongate slots in the wall of the plunger, so that the tongues are in position behind the tampon. The applicator is readied for being used by retraction of the plunger rearwardly to cause the tampon, which is restrained by the tongues, to be ejected from the plunger into the barrel. The tongues also serve to prevent the plunger from separating from the barrel. The front of the plunger collapses inwardly to form an effective tampon contacting surface for engaging the rear of the tampon in a manner which permits the plunger to push the tampon out of the barrel. Subsequent forward actuation of the plunger expels the tampon through the front of the barrel into the catamenial canal.

19 Claims, 2 Drawing Sheets

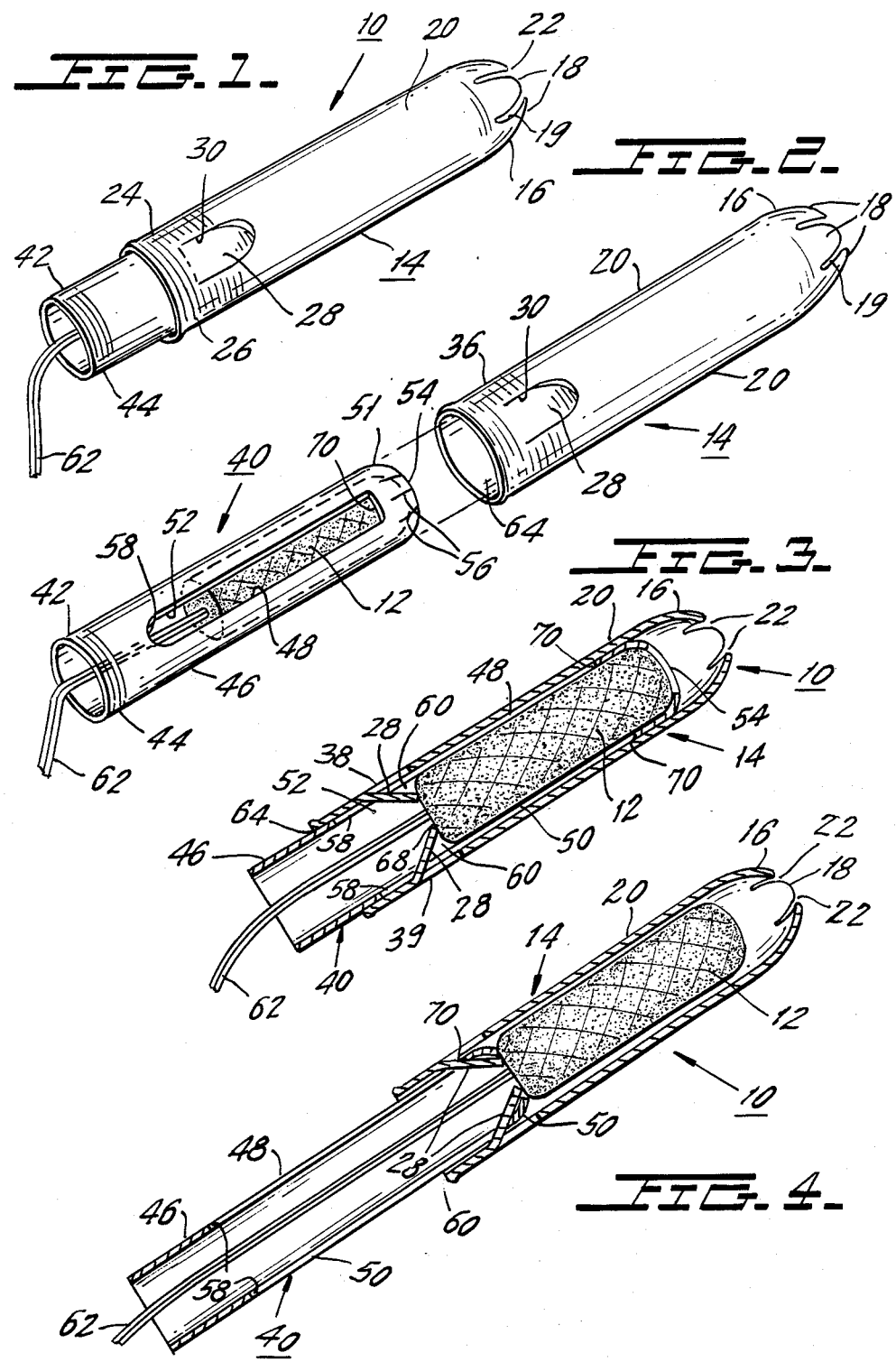

PORTABLE TAMPON APPLICATOR

BACKGROUND OF THE INVENTION

The present invention relates to a tampon applicator and, more particularly, to a preferably short and compact applicator in which the tampon is initially positioned within a plunger and is ejected from the plunger and the plunger is subsequently used for ejecting the tampon from the applicator into the catamenial canal.

Different styles of applicators for introducing catamenial tampons intravaginally are available. Manufacturers of these applicators strive to make applicators simpler, easier to use and at the same time less expensive in order to obtain even minute advantages over competitive devices. A small saving in the manufacture of an applicator can translate into substantial profits in view of the high annual volume of tampon applicators.

The present invention is generally directed to the type of tampon applicators which have an outer, cylindrical barrel which holds an absorbent tampon for being ejected into the catamenial canal. The tampon is ejected by a cylindrical plunger that is positioned behind the tampon in the barrel. The plunger diameter is somewhat smaller than that of the barrel. The plunger slides within the barrel for ejecting the tampon out the front of the barrel. Once the tampon has been ejected, the applicator is withdrawn and discarded.

The present invention is generally directed to the type of applicator which is described in U.S. Pat. No. 4,286,595 to Ring (the '595 patent). The '595 patent provides a shorter length applicator wherein the tampon is disposed within the plunger, permitting almost the entire body of the plunger to be received within the barrel. The resulting applicator is about one-half as long as conventional applicators.

The applicator is readied for use by retracting the plunger to position the plunger behind the tampon. To prevent the tampon from moving rearwardly with the plunger, one or more restraining elements project inward from the barrel, through elongate slots in the plunger, into the interior of the plunger. Thus, retraction of the plunger draws the tampon out of and positions it in front of the plunger. Subsequent forward actuation of the plunger pushes the tampon out of the barrel into the catamenial canal. In addition, the restraining elements limit the rearward movement of the plunger to prevent it from separating from the barrel. The present invention improves upon such retractable applicators.

The applicator of the '595 patent has first and second main embodiments. The first embodiment provides an outer barrel 14 and a single integrally molded restraining element 28 which projects from the rim or ring 20 of barrel 14 and reaches a considerable distance radially inwardly in order to engage the center region of a tampon 16. The restraining element is relatively thick and not easily capable of being flexed against the inner wall surface of barrel 14. The restraining element complicates manufacture of the barrel and makes it more difficult to assemble the plunger in the barrel. Further, the restraining element is unsuitable for being supported on or molded directly from the relatively thin wall of barrel 14. It requires the relatively thick and sturdy rim 20 to support it and this further restricts the ability to locate the restraining element at more suitable and effective locations relative to the barrel.

In place of restraining element 28, the second embodiment of the '595 patent provides a pair of tabs 50, seen in FIG. 5 of the '595 patent. Tabs 50 extend mainly along the wall of barrel 14, instead of projecting into the interior of the plunger Consequently, the tabs may scrape off the outer periphery of the tampon rather than restraining it from moving back with the plunger, particularly if the tampon is held tightly by the plunger. Further, these tabs are complicated and costly to manufacture.

The '595 patent also provides a friction grip on the outer surface of the barrel to prevent the barrel from slipping between the fingers of the user. The restraining element or tabs of the '595 patent do not contribute to improve grasping of the applicator.

Great Britain Pat. No. 684,290 shows two juxtaposed deformations for interlocking a barrel and a plunger of a tampon applicator. The deformations provide a finger abutment.

U.S. Pat. No. 3,645,263 shows, in FIGS. 3-5 thereof, the use of at least one triangular shaped tab 26 to lock a barrel with a plunger. The tabs are formed by a portion of the wall of the outer barrel which is punched inwardly to penetrate through the plunger. The resulting perforations in the wall of the barrel are usable as friction grasping aids for holding the barrel.

U.S. Pat. No. 2,587,717 provides a tongue 12 on the barrel to engage an edge portion of an inner tube which corresponds to the above plunger. A roughened surface 6 provides a finger grip.

U.S. Pat. No. 3,101,713 uses elements 20 as tabs which project into slots 18 of a plunger to prevent it from separating from an outer barrel. Separate restraining elements 32 serve to retain the tampon in place while the plunger is being retracted.

U.S. Pat. No. 4,699,610 provides a projection 23 on the inner surface of the barrel to act as a stop for a tampon and as a restraining device which engages in a slot 24 of the plunger to prevent its complete retraction from the barrel.

U.S. Pat. No. 4,276,881 uses a series of stops and compressible flanges in an inner plunger tube to prevent complete retraction of the plunger and to eject the tampon from the plunger during retraction of the plunger.

U.S. Pat. No. 4,291,696 issued to the inventor of the '595 patent describes ribs 31 which function as the aforementioned restraining element.

Additional art on the subject matter of the present invention includes U.S. Pat. Nos. 4,676,773; 4,479,791; 4,273,125; 4,329,991; 4,411,647; 4,498,899; 4,543,086; 4,650,459; 4,726,805; Great Britain Patent Application No. 2,033,754 A; and EPO Publication No. 223,072.

However, while the prior art has recognized the advantages of a compact and short applicator and has provided various embodiments thereof, the inventors herein have conceived further improvements which result in an applicator which is simpler and more easily and economically manufactured.

SUMMARY OF THE INVENTION

Accordingly, it is an object of the present invention to provide a compact tampon applicator which is simple to fabricate and use.

It is another object of the present invention to provide a compact tampon applicator which realizes the functions of separating the tampon from the plunger, preventing the plunger from falling from the barrel and permitting a firm grasp on the barrel, all by means of a single pair of easily formed elements It is yet another object of the present invention to provide a compact tampon applicator which can be readily fabricated of either plastic, cardboard, or of combinations of these materials.

The foregoing and other objects of the invention are attained with a compact and short tampon applicator which is formed of an outer barrel which surrounds a tampon holding inner plunger. The plunger is hollow, cylindrical in cross-section, and defined by a peripheral wall having a pair of elongate slots on opposite sides. The slots extend longitudinally from near the front-/ejecting end of the plunger toward the opposite, gripping end of the plunger. After its fabrication, the plunger is loaded with a tampon, the tampon extending from the ejecting end toward but short of the termination end of the slots, nearer the gripping end.

The barrel is cylindrically shaped and is sized to fit tightly around the plunger, but loose enough that the plunger can slide within the barrel. The barrel has an insertion end and a barrel grasping end. The wall of the barrel nearer the grasping end is punched radially in, at two diametrically opposed locations, to form first and second tongue type elements. The tongues in the barrel are aligned with and are sized to fit into the slots of the plunger and the tongues are deflected inwardly through the slots into the interior of the plunger, behind the tampon. Thus, the tongues simply punched from the wall of the barrel are effective for ejecting the tampon from the plunger as the plunger is retracted rearwardly in the barrel and also for preventing the plunger from separating from the barrel during retraction. In addition, the punching of the tongues from the wall of the barrel leaves behind a pair of depressions by which the barrel can be securely grasped during use.

Other features and advantages of the present invention will become apparent from the following description of the invention which refers to the accompanying drawings.

BRIEF DESCRIPTION OF THE DRAWINGS

FIG. 1 is a perspective of an assembled compact tampon applicator in accordance with the present invention.

FIG. 2 is an exploded view showing the tampon applicator of FIG. 1 with the plunger separated from the outer barrel.

FIG. 3 is a longitudinal cross-section through the tampon applicator of FIG. 1.

FIG. 4 is a cross-section showing the tampon applicator of FIG. 1 with the plunger positioned for ejecting the tampon from the barrel.

DESCRIPTION OF THE PREFERRED EMBODIMENTS

Figure 5:
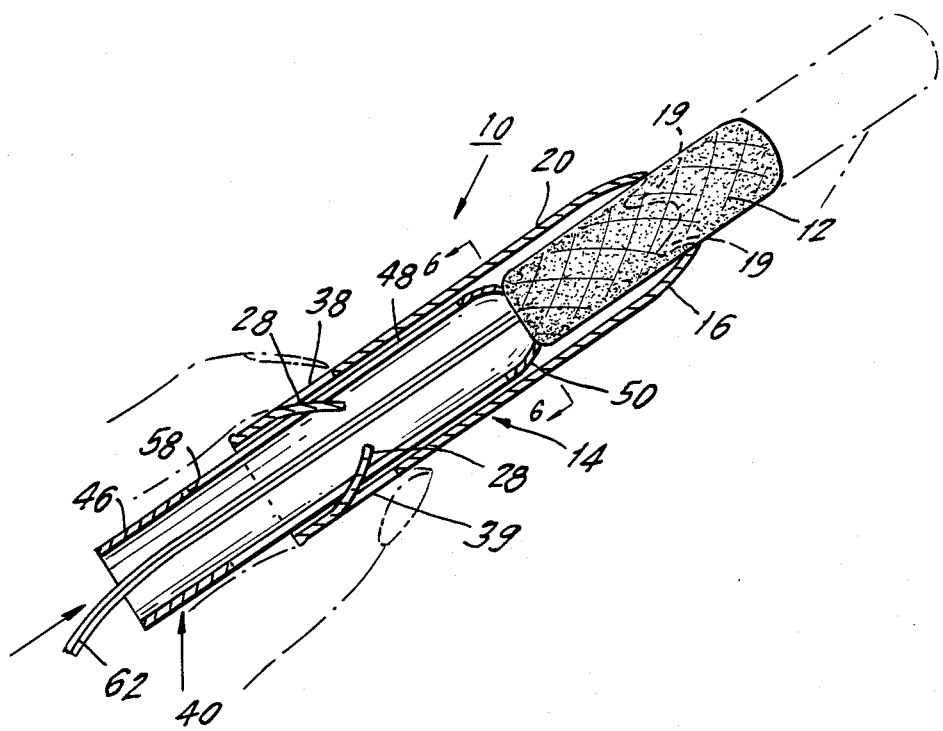
FIG. 5 shows the tampon applicator in a state with the tampon partially ejected from the barrel.

The catamenial device of the present invention comprises a tampon applicator 10, which contains and enables insertion within the catamenial canal of an absorbent catamenial tampon or pledget 12.

Tampon applicator 10 is formed of an elongate, generally cylindrical, outer barrel 14 which has a forward end which curves radially inwardly to form an insertion tip 16. Insertion tip 16 has a general hemispherical dome shape and is formed from triangular petal-like segments 18 which are integrally formed from the forward end region of the wall 20 of barrel 14.

The material of which barrel 14 is comprised is not critical, and various materials, such as cardboard and plastics, have been widely used in the past. Plastics and particularly thermoplastics are especially suitable for forming an insertion tip that will keep its dome shape and yet permit the segments 18 to uncurl relatively easily into an opening as large as the diameter of barrel 14, in response to a relatively slight pressure exerted on the segments from within barrel 14 by tampon 12. The number, size and shape of these triangular segments are selected to yield an insertion tip of a desired configuration. Preferably, four triangular segments are employed. They are shaped to converge in a manner which minimizes the spaces 19 between the individual segments 18 and forms the desired shape without segments 18 overlapping along their sides or at their tips 22. Additionally, the tips 22 are preferably rounded to ease insertion.

To enable a good grip on barrel 14, a plurality of spaced circumferential ribs 24 are provided at the rear gripping region 36 on barrel 14. Alternatively, a series of lines 26 are scored or stamped into the outer surface of wall 20 of barrel 14 to roughen the surface to improve the grip on barrel 14. The barrel is tubular and of uniform cross-sectional thickness between its opposed grasping end 36 and insertion end 16.

Barrel 14 is completed with the formation of at least one tongue 28 and, preferably, a pair of tongues 28 which are spaced 180° apart on opposite sides of the wall 20 of barrel 14 and formed of the material constituting the tubular barrel wall. Each tongue 28 is formed by slitting, cutting or molding a pair of longitudinally extending cuts and a forward terminus cut, as shown by the U-shaped slit 30 in the wall 20 of barrel 14. The base of the U-shaped slit lies nearer the insertion tip 16 of barrel 14 such tongue 28 is cantilevered towards the insertion end 16 of the barrel. The tongues 28 are the same thickness as the uniform cross sectional thickness material of the barrel wall, overly the area defined by the cuts forming the u-shape slit 30, and form an acute angle with respect to the insertion end 16 of the barrel. Thermoplastically, or by any other known means, tongues 28 are then deflected into the interior 32 of barrel 14. Formation of tongues 28 in the aforementioned manner inherently produces a pair of finger accommodating depressions 38 and 39 for enabling gripping of barrel 14.

The simply formed tongues 28 perform the multiple functions of restraining tampon 12 during retraction of a plunger 40, and locking plunger 40 to prevent it from slipping out of barrel 14. Advantageously it may also provide a better finger grip on barrel 14.

The plunger 40 is cylindrically shaped and sized to hold in its interior 52 the catamenial tampon 12. To be readied for use, the tampon is separated from the plunger 40 and the plunger is deployed for pushing tampon 12 from barrel 14 into the catamenial canal. The somewhat longer plunger 40 slides within barrel 14 and has a gripping end 42 which projects slightly beyond the rear open end of barrel 14. As seen in FIG. 3, gripping end 42 of plunger 40 contains closely spaced circumscribing tabs or score lines 44 similar to lines 24 on barrel 14. The wall 46 of plunger 40 is partially cut away to form at least one but preferably a pair of slots 48 and 50 spaced 180° on opposite sides around the plunger. The slots 48 and 50 extend from about the ejecting end 51 of plunger 40 to its gripping end 42 and each slot has a distal edge 70 and a proximal edge 58. The slots 48 and 50 are sufficiently wide to permit tongues 28 of barrel 14 to pass therethrough in non-interference relationship with respect to the outer wall of the plunger 40, into the interior 52 of plunger 40, behind tampon 12.

Figure 6:
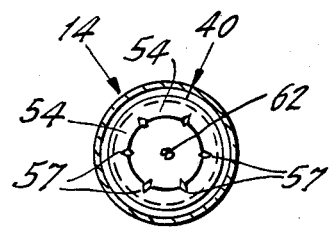
FIG. 6 is a front view of the plunger as seen along line 6—6 in FIG. 5, depicting a variant embodiment in which a tampon contacting surface of the plunger is formed by folds located in the forward terminus of the plunger.

The wall 46 of plunger 40, at ejecting end 51, is constricted inwardly as seen in FIGS. 2, 4 and 6 to form a resilient tampon contacting surface 54 for bearing on tampon 12 as tampon 12 is pushed out of barrel 14 through insertion tip 12. Tampon contacting surface 54 may be formed thermoplastically, if plunger 40 is fabricated of thermoplastic material. It may also be formed by means of circumferentially spaced slits 56 (FIG. 2) which cut the forward terminus of wall 46 into small segments or petals that are flexibly collapsed and biased radially inwardly to form the tampon contacting surface 54. Alternatively, as seen in FIG. 6, the forward terminus of wall 46 contains a plurality of inwardly directed and equally spaced indentations or folds 57 for forming a tampon contact surface 54 which is stronger/sturdier and easier to manufacture. Preferably, there are 6–10 such indentations/folds 57 which folds 57 expand during tampon ejection and retract following tampon ejection from plunger 40 as described below.

Catamenial tampon 12 is assembled within plunger 40 with its forward end lying about flush inside the ejection end 51 of plunger 40. But, if desired, the forward end of tampon 12 may project slightly from plunger 40. The opposite end of tampon 12 reaches near but short of the proximal edges 58 of slots 48 and 50.

The bodies of plunger 40 and barrel 14 are angularly aligned to register the tongues 28 of barrel 14 with slots 48 and 50 of plunger 40. This enables tongues 28 to project into the unobstructed portion 60 of slots 48 and 50 behind tampon 12. Alternately, tongues 28 may be formed to stay flush with the wall 20 of barrel 14 initially and to be subsequently deflected into the interior 52 after plunger 10 is positioned in barrel 14. Another possibility is to insert tampon 12 into the distal end of the plunger subsequent to the assembly of plunger 40 in barrel 14.

The assembled applicator 10, as seen in FIG. 3, supports tampon 12 generally forwardly in barrel 14, with only the relatively short gripping end 42 of plunger 40 and withdrawal string 62 of tampon 12 projecting from its rear opening 64.

Applicator 10 of the present invention is readied for use by gripping plunger 40 with one hand and barrel 14 by the other hand and retracting plunger 40 to the retracted position of FIG. 4. During retraction, tampon 12 is prevented from moving with plunger 40 by the tongues 28 which bear against the rear 68 of tampon 12. At the end of travel of plunger 40 tampon 12 will have been ejected from the interior 52 of plunger 40, permitting tampon contacting surface 54 of plunger 40 to collapse radially inwardly to form a solid contacting surface for bearing against the rear of tampon 12 and readying the tampon for insertion.

Moreover, further retraction of plunger 40 results in the snagging of the distal edges 70 of slots 48 and 50 of plunger 40 by the tongues 28. This prevents plunger 40 from separating from barrel 14.

Next, barrel 14 is inserted in the catamenial canal and plunger 40 is pushed forward to eject tampon 12 through the flexible and easily yielding triangular segments 18 of the insertion tip 16 of barrel 14. FIG. 5 shows how the inwardly biased triangular segments 18 of barrel 14 press tightly against tampon 12 while the tampon is being ejected. This prevents the pinching of sensitive tissue or other discomfort during the insertion process.

Once tampon 12 has been ejected entirely from barrel 14, triangular segments 18 will either reconverge to a tip or adhere to the outer surface of plunger 40. In either case, withdrawal of barrel 14 will be free of scraping and discomfort.

Barrel 14 and plunger 40 of the tampon applicator assembly 10 of the present invention may be constructed of materials such as synthetic polymers, cardboard, other biodegradable materials, or the like. For example, barrel 14 may be formed of relatively more rigid plastic while plunger 40 is formed of cardboard, or vice versa, or they may be formed of like material. Thermoplastics, and particularly, polyolefins are preferred materials for construction of the tampon applicator of the present invention, with polyethylene being particularly preferred due to its low cost and ease of molding. Thermoplastics are probably best for forming the collapsible insertion tip 16 of barrel 14 of the present invention.

The manufacturing process for barrel 14 and plunger 40 may be in accordance with the teachings of U.S. Pat. No. 3,895,634 assigned to the assignee of the instant application, the contents of which are incorporated by reference. It may be noted that the ejection end 51 of plunger 40 may be formed in accordance with the teachings described in the aforementioned art in relation to the formation of insertion tip 12 of the barrel 14. The tongues 28 may also be thermoplastically set to project into barrel 14.

Although the present invention has been described in relation to a particular embodiment thereof, many other variations and modifications and other uses will become apparent to those skilled in the art. It is preferred, therefore, that the present invention be limited not by the specific disclosure herein, but only by the appended claims.

What is claimed is:

1. In a tampon applicator, comprising: a hollow cylindrical barrel having interior and outer cylindrical walls extending between opposed insertion and barrel grasping ends, and a hollow cylindrical plunger telescopically slidable within said barrel between first and second positions;

said plunger having outer and interior cylindrical walls, extending between opposed tampon ejecting and actuating ends, said plunger interior cylindrical wall initially holding a tampon therein at said first position, said tampon ejecting end abutting the rear end of the tampon at said second position for pushing the tampon, and said actuating end being manually movable towards said barrel insertion end to urge said tampon ejecting end against the rear end of the tampon to eject the tampon from the insertion end of the barrel;

at least one closed ended elongate slot in the plunger wall which extends from adjacent the ejection end of the plunger towards the actuating end; and the improvement comprising said barrel being of substantially uniform cross sectional thickness between is opposed insertion and barrel grasping ends, at least one slit positioned along and extending through the tubular cylindrical barrel, said slit including a pair of longitudinally opposed cuts extending from a first end adjacent the barrel grasping end to a second end in the direction of the barrel ejection end and a forward terminus cut at said second end to define therebetween a tongue integrally formed from and being of the same thickness as the uniform cross section thickness material of the tubular barrel wall, said tongue overlying the area defined by said pair of longitudinally opposed and forward terminus cuts and cantilevered forwardly towards the insertion end of the barrel from its connection to the barrel at said first end of the longitudinally opposed cuts, said tongue forming an acute angle with respect to, the insertion end of the barrel and deflected inwardly into the interior of the plunger through said elongate slot, in non-interference relationship with respect to the outer cylindrical wall of the plunger, the deflected tongue being effective in said first position for restraining the tampon against rearward movement and for ejecting the tampon from the plunger as the plunger is being retracted from the barrel toward said second position and for engaging the closed end of the elongate plunger slot to prevent the plunger from separating from the barrel during retraction of the plunger.

2. The applicator of claim 1, wherein the tongue is defined by a U-shaped cut in the barrel wall and the tongue is indented inwardly.

3. The applicator of claim 2, wherein the tampon extends from adjacent the ejecting end of the plunger toward but not to the end of the slot in the plunger.

4. The applicator of claim 3, wherein the cut portion of the barrel wall defines a finger grip on the barrel.

5. The applicator of claim 4, wherein the finger grip is U-shaped and the base of the U-shaped finger grip lies nearer the insertion end of the barrel.

6. The applicator of claim 3, wherein there are first and second ones of the at least one tongue and there are respective first and second ones of the at least one slot, the first and second tongues are in registration, respectively, with the first and second slots.

7. The applicator of claim 7, in which the first and second tongues and the respective first and second slots are on opposite sides of the applicator.

8. The applicator of claim 7, wherein the barrel includes an insertion tip at the insertion end.

9. The applicator of claim 8, wherein the insertion tip comprises a forward terminus of the barrel wall which is formed into a plurality of generally triangular resilient segments, which are deflected radially inwardly to form a generally closed smooth insertion tip.

10. The applicator of claim 9, wherein the triangular segments have rounded free ends.

11. The applicator of claim 1, further comprising grip lines on the grasping end of the barrel.

12. The applicator of claim 1, further including grip lines on the actuating end of the plunger.

13. The applicator of claim 1, the plunger having a tampon contacting surface formed of a forward portion of the wall of the plunger which is bent radially inwardly.

14. The applicator of claim 13, comprising a plurality of slits in the forward portion of the wall of the plunger for forming the tampon contacting surface.

15. The applicator of claim 13, comprising a plurality of spaced folds in the forward portion of the wall of the plunger to form the tampon contacting surface.

16. The applicator of claim 1, wherein the barrel is formed of a synthetic thermoplastic material.

17. The applicator of claim 16, wherein the tongues are thermoplastically set to project into the interior of the barrel.

18. The applicator of claim 1, wherein the plunger and barrel are formed of cardboard material.

19. The applicator of claim 1, wherein one of the barrel and the plunger is formed of a synthetic material and the other one of the barrel and plunger is formed of a biodegradable material.

* * * * *